United States Patent
Hong et al.

(10) Patent No.: US 8,237,925 B2
(45) Date of Patent: Aug. 7, 2012

(54) PRISM FOR INDUCING BREWSTER'S ANGLE TRANSMISSION AND FLUORESCENCE DETECTION APPARATUS FOR IMPROVING SIGNAL-TO NOISE RATIO USING THEREOF

(75) Inventors: Youngjoo Hong, Gangwon-do (KR); Jeongho Ahn, Daejeon (KR); Hyojun Park, Jeollabuk-do (KR); Hyungchul Lee, Daejeon (KR); Sungyoon Ryu, Busan (KR); Wonsik Kwon, Jeollabuk-do (KR); Soohyun Kim, Daejeon (KR)

(73) Assignee: Korea Advanced Institute of Science and Technology (KR)

( * ) Notice: Subject to any disclaimer, the term of this patent is extended or adjusted under 35 U.S.C. 154(b) by 364 days.

(21) Appl. No.: 12/578,639

(22) Filed: Oct. 14, 2009

(65) Prior Publication Data
US 2010/0225915 A1 Sep. 9, 2010

(30) Foreign Application Priority Data
Mar. 4, 2009 (KR) .................. 10-2009-0018612

(51) Int. Cl.
*G01J 4/00* (2006.01)

(52) U.S. Cl. ..................... 356/369; 356/445

(58) Field of Classification Search .......... 356/369, 356/364, 445
See application file for complete search history.

(56) References Cited

U.S. PATENT DOCUMENTS

| | | | | |
|---|---|---|---|---|
| 5,437,840 A | * | 8/1995 | King et al. | 422/82.08 |
| 5,538,850 A | * | 7/1996 | King et al. | 435/6.12 |
| 5,986,768 A | * | 11/1999 | Pipino | 356/440 |
| 6,859,280 B2 | * | 2/2005 | Kempen | 356/369 |

FOREIGN PATENT DOCUMENTS

| | | |
|---|---|---|
| JP | 10-078390 A | 3/1998 |
| JP | 3562912 B2 | 8/2004 |
| JP | 2007-078451 A | 3/2007 |
| KR | 1020060089103 A | 8/2006 |
| KR | 100768038 B1 | 10/2007 |

OTHER PUBLICATIONS

Korean Patent Office, "Korean Office Action for Korean International Application No. 10-2009-0018612", Dated: Jan. 28, 2011, Publisher: Korean Patent Office, Published in: KR.

* cited by examiner

*Primary Examiner* — Roy M Punnoose
(74) *Attorney, Agent, or Firm* — Kaplan Breyer Schwarz & Ottesen LLP

(57) ABSTRACT

The present invention relates to a prism for inducing Brewster's angle transmission and a fluorescence detection apparatus for enhancing a signal-to-noise ratio using thereof, and more specifically, to a prism for inducing Brewster's angle transmission and a fluorescence detection apparatus for enhancing a signal-to-noise ratio using thereof, in which evanescent waves are generated when light is cast onto fluorescence material applied on a sample surface at an angle greater than a critical angle, and the evanescent waves are used as excitation light of fluorescence to induce total internal reflection of the light so that the light may pass through the prism at a Brewster's angle. Therefore, effects of the re-reflected light on the sample surface are removed, and a signal-to-noise ratio (SNR) is improved at the same time. In addition, the prism is miniaturized, and therefore, usage of the sample area and efficiency of the light amount are improved.

12 Claims, 2 Drawing Sheets

PRISM FOR INDUCING BREWSTER'S ANGLE TRANSMISSION AND FLUORESCENCE DETECTION APPARATUS FOR IMPROVING SIGNAL-TO NOISE RATIO USING THEREOF

FIELD OF THE INVENTION

The present invention relates to a prism for inducing Brewster's angle transmission and a fluorescence detection apparatus for enhancing a signal-to-noise ratio using thereof, and more specifically, to a prism for inducing Brewster's angle transmission and a fluorescence detection apparatus for enhancing a signal-to-noise ratio using thereof, in which light linearly polarized in parallel to the incident plane enters into the prism and excites fluorescence material using evanescent waves generated on condition of total internal reflection, and the total-internal-reflected light generating the evanescent waves passes through the prism at a Brewster's angle when it goes out of the prism, thereby improving a signal-to-noise ratio by removing a component re-reflected into the prism.

BACKGROUND OF THE INVENTION

Generally, a fluorescence measuring method is a method of measuring the degree of reaction of a sample by previously adding a marker labeled with a fluorescence substance to a sample, irradiating light on the sample, and sensing change of the amount of fluorescence.

Such a conventional fluorescence measuring technique has a problem in that loss of fluorescence is severe since only some of the fluorescence radiated from the sample arrives at an optical detector.

Therefore, the loss of fluorescence inevitably increases the bound of ability for detecting minimum fluorescence as a result, and thus there is a problem in that measurement is not allowed in an experiment that requires high sensitivity since sensitivity is degraded.

Furthermore, since a mixture of excitation light of the fluorescence and reactive fluorescence is detected by the optical detector due to a reason of light path, there is a problem in that the signal-to-noise ratio is not sufficiently high.

Korea Patent Registration No. 10-0768038 (hereinafter, referred to as "conventional patent 1") and Korea Patent Publication No. 10-2006-0089103 (hereinafter, referred to as "conventional patent 2") have been applied to solve such problems. However, loss of light is too severe to input excitation light into a plate-shape optical waveguide using a diffusion plate, and there is a proportional relationship between utilization of light amount and distance between samples when evanescent waves are generated and excite fluorescence material in the optical waveguide.

Here, since the light total-internal-reflected from the sample surface generates evanescent waves on the next sample surface after being total-internal-reflected from the opposite side of the sample surface, thickness of the optical waveguide should be formed as thin as possible in order to densely arrange the samples on the sample surface.

However, those are disadvantageous in that as the optical waveguide is the thinner, optical loss is the higher. If a thick optical waveguide is used in order to reduce the optical loss, there is a problem in that the sample surface cannot be efficiently used since the distance between the samples is extended.

In addition, since conventional patents 1 and 2 use the evanescent waves sequentially generated along the optical waveguide, it is inappropriate to measure change of the amount of fluorescence since the amount of light that excites following fluorescence materials is changed depending on the degree of excitation of the first reacting fluorescence material.

SUMMARY OF THE INVENTION

Therefore, the present invention has been made in view of the above problems, and the objects of the present invention are as follows.

First, an object of the present invention is to detect fluorescence using evanescent waves of a prism for inducing Brewster's angle transmission.

Second, another object of the present invention is to form a thin prism while uniformly radiating a wide area of a sample.

Third, another object of the present invention is to miniaturize the prism for inducing Brewster's angle transmission by forming a thin prism.

Fourth, another object of the present invention is to provide a fluorescence detection apparatus for improving a signal-to-noise ratio.

Technical means for accomplishing the above objects of the present invention are described below.

In a prism for inducing light linearly polarized in parallel to an incident plane to enter the prism, generate evanescent waves by total internal reflection, and pass through the prism at a Brewster's angle so as not to have a component that is re-reflected into the prism and passes through a sample surface, the prism comprises an incident surface formed at a first end on a lower side of the sample surface and a transmission surface formed at a second end on the lower side from a viewpoint of a side cross-sectional direction, in which the incident surface is perpendicular to the transmission surface at a contacting position.

The incident surface of the prism is formed to be perpendicular to an incident angle of excitation light. The angle between the incident surface and the transmission surface is formed as prism angle 2, and the prism angle 2 is 90°.

The angle between the sample surface and the transmission surface of the prism is formed as prism angle 1, and the prism angle 1 is formed by mathematical expression $\theta_{p1}=(90°-\theta_B)/2$. Here, $\theta_B$ is the Brewster's angle.

An angle between the sample surface and the incident surface is formed as prism angle 3, and the prism angle 3 is formed by mathematical expression $\theta_{p3}=(90°+\theta_B)/2$. Here, $\theta_B$ is the Brewster's angle.

The Brewster's angle is formed by mathematical expression $\theta_B=\arctan(n_a/n_p)$. Here, $n_a$ is the refractive index of air, and $n_p$ is the refractive index of the prism.

On the other hand, in a fluorescence detection apparatus using evanescent waves of a prism for inducing Brewster's angle transmission, the fluorescence detection apparatus comprises: a light source unit for providing a light source; a prism unit formed at one side of the light source unit and having a prism for generating the evanescent waves by total internal reflection; a sample unit formed at one side of the prism unit and having a sample-measuring tube for providing fluorescent protein and a sample applied with the fluorescent protein; and a detection unit formed at one side of the sample unit, for detecting an amount of fluorescence depending on a reaction of the fluorescent protein and the sample using the evanescent waves.

The light source unit includes: the light source for providing emissive light; a collimating optical device formed at one side of the light source, for providing collimated light; and a linear polarizer formed at one side of the collimating optical device, for providing excitation light.

The collimating optical device is formed to input the collimated light in the direction perpendicular to an incident surface of the prism, and the linear polarizer is formed between the prism and the collimating optical device to be parallel to the incident surface of the prism.

The prism unit is formed to repeatedly arrange a plurality of prisms on the sample surface formed on the bottom of the sample-measuring tube.

The detection unit includes: an optical device formed at one side of the sample-measuring tube of the sample unit, for passing through fluorescent detection light provided by the sample-measuring tube; and a detector for calculating the fluorescent detection light provided by the optical device.

BRIEF DESCRIPTION OF THE DRAWINGS

The above and other objects, features and advantages of the present invention will be apparent from the following detailed description of the preferred embodiments of the invention in conjunction with the accompanying drawings. The present invention is not to be restricted by those shown in the figures.

DETAILED DESCRIPTION

The preferred embodiments of the invention will be hereafter described in detail, with reference to the accompanying drawings.

Configuration of a Prism According to the Present Invention>

Figure 1:
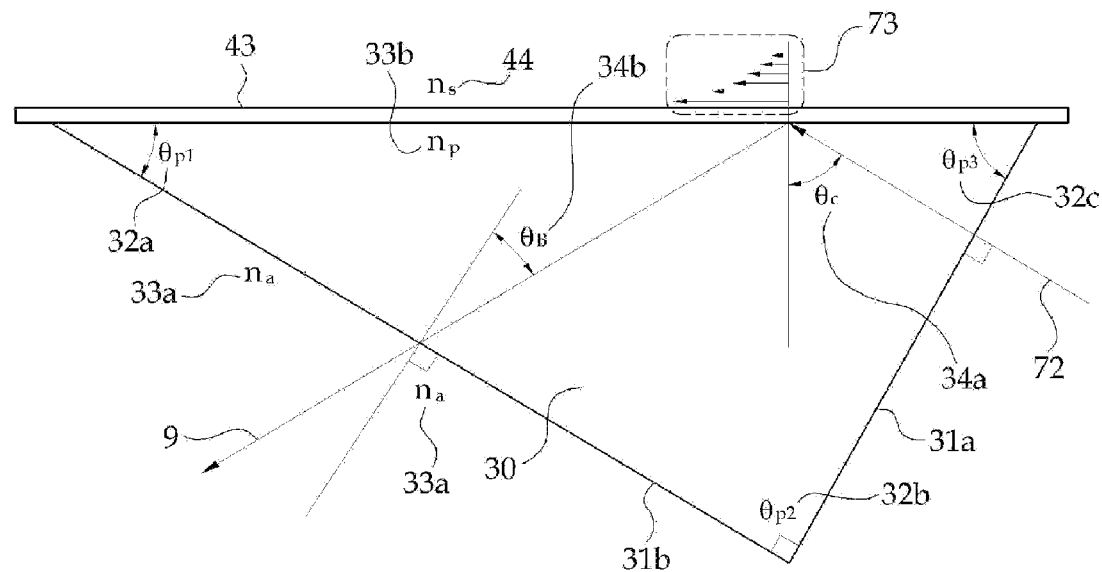
FIG. 1 is a side cross-sectional view showing the operational state of a prism for inducing Brewster's angle transmission according to the present invention.

FIG. 1 is a side cross-sectional view showing the operational state of a prism for inducing Brewster's angle transmission according to the present invention. As shown in FIG. 1, the prism for inducing Brewster's angle transmission according to the present invention is configured to induce light linearly polarized in parallel to the incident plane to enter the prism, generate evanescent waves by total internal reflection, and pass through the prism at a Brewster's angle so as not to have a component that is re-reflected into the prism and passes through the sample surface.

To this end, the prism 30 according to the invention has an incident surface 31a formed at a first end on a lower side of a sample surface 43 and a transmission surface 31b formed at a second end on the lower side from the viewpoint of a side cross-sectional direction, and the incident surface 31a is perpendicular to the transmission surface 31b at the contacting position.

Here, the incident surface 31a is an incident surface 31a of excitation light 7 of a medium, and the transmission surface 31b is a transmission surface 31b of the medium after total internal reflection.

(Conditions for Forming the Prism According to the Present Invention)

The shape of the prism 30 according to the present invention is determined on the conditions described below.

Condition 1 is that light enters into the prism in the direction perpendicular to the incident surface 31a in order to maximize transmittance of the excitation light 72.

Condition 2 is that prism angle 2 32b between the incident surface 31a and the transmission surface 31b of the prism has a right angle so that a prism 30 may not cast a shadow on neighboring prisms or the excitation light 72 may not enter into the transmission surface 31b of the prism.

Condition 3 is that prism angle 1 32a is formed between the sample surface 43 and the transmission surface 31b so that the transmitted light 9 traveling to the transmission surface 31b of the prism after total internal reflection may have a Brewster's angle 34b with respect to the refractive indexes 33b and 33a of the prism and air.

Condition 4 is that prism angle 3 32c is formed to be equal to or greater than a critical angle since the total internal reflection angle 34a becomes to be equal to the prism angle 3 32c on the sample surface by condition 1.

It is preferable that the refractive index 33b of the prism 30 is set to satisfy conditions 3 and 4 described above.

(Induction of Evanescent Waves of the Prism of the Present Invention)

It is induced to generate evanescent waves on the sample surface by inputting light at an angle equal to or greater than a critical angle so that total internal reflection may occur on the sample surface 43 of the prism 30 applied with a fluorescence material and thus the fluorescence material may be excited by the evanescent waves.

When light passes through a boundary surface of two different media, incident and transmission angles according to the refractive indexes of the media follow Snell's law. Refractive index $n_1$ and incident angle $\theta_1$ of medium 1 and refractive index $n_2$ and incident angle $\theta_2$ of medium 2 have a relation as shown in mathematical expression 1.

$$n_1 \sin\theta_1 = n_2 \sin\theta_2 \quad \text{[Mathematical expression 1]}$$

A critical angle where the total internal reflection starts to occur when $n_1 > n_2$ is defined as shown in mathematical expression 2.

$$\sin\theta_c = n_2/n_1 \quad \text{[Mathematical expression 2]}$$

Here, $\theta_c$ denotes the critical angle, $n_2$ denotes the refractive index of medium 2, and $n_1$ denotes the refractive index of medium 1.

That is, when incident angle $\theta_1$ is critical angle $\theta_c$ in medium 1, it can be assumed that refractive angle is $\theta_2=90°$ in medium 2, and the phenomenon where light is not refracted into medium 2 but totally reflected is referred to as total internal reflection.

A standing wave referred to as an evanescent wave is formed on the boundary surface of the media on conditions of the total internal reflection described above. The evanescent wave on the boundary surface of the media is defined as shown in mathematical expression 3.

$$E(r) = E_o e^{-i k \cdot r} = E_0 e^{-\alpha y - i\beta z} \quad \text{[Mathematical expression 3]}$$

Here, E(r) denotes the evanescent wave, $E_o$ denotes the amplitude of the incident light, y denotes the vertical direction of the boundary of media, $\alpha$ denotes an attenuation constant, denotes the horizontal direction, and $\beta$ denotes a propagation constant. At this point, since the evanescent wave exists within about 100 nm in the neighborhood of the boundary surface of the media, only the fluorescence material thinly applied on the sample surface is effectively excited.

(Brewster's Angle Transmission of the Prism According To the Present Invention)

When the light linearly polarized in parallel to the incident plane passes through the boundary surface of the media, reflection components are removed if the light enters into the prism at the Brewster's angle. The condition for being the Brewster's angle is as shown in mathematical expression 4 according to the transmission/reflection law in Fresnel equations.

$$\theta_1 + \theta_2 = 90° \quad \text{[Mathematical expression 4]}$$

$\theta_1$ denotes the incident angle, and $\theta_2$ denotes the transmission angle. If $\theta_1$ and $\theta_2$ are put into the Snell's law and evaluated, the Brewster's angle can be expressed as shown in mathematical expression 5.

$$\theta_B = \arctan(n_2/n_1) \quad \text{[Mathematical expression 5]}$$

Here, $\theta_B$ denotes the Brewster's angle, $n_2$ denotes the refractive index of medium 2, and $n_1$ denotes the refractive index of medium 1.

Since the total-internal-reflected light passes through the prism at a Brewster's angle, the components re-reflected into the prism can be removed, and effects of the light re-reflected within the prism upon the sample surface can be removed thereby.

(Design of Prism Angles for Miniaturizing and Patterning of the Prism According to the Invention)

When the prism for inducing Brewster's angle transmission is miniaturized and formed as a pattern according to the invention, useless shadowed portions do not occur although the prism 30 is formed as a pattern on condition that the incident surface 31*a* of the prism 30 which receives the incident light is perpendicular to the propagation direction of the incident light and the transmission surface 31*b* of the prism 30 through which the light passes through after total internal reflection is parallel to the direction of the incident light.

Accordingly, when prism angle 2 32*b* $\theta_{p2}$ of FIG. 1 is 90°, all the light entering in parallel to the prism 30 pattern can be used to generate evanescent waves 73.

With respect to the refractive index $n_a$ of air, refractive index $n_s$ of the sample, and refractive index $n_p$ of the prism of FIG. 1, the degree of the Brewster's angle for satisfying the conditions of mathematical expressions 1 and 2 can be defined as shown in mathematical expression 6.

$$\theta_B = \arctan(n_a/n_p) \quad \text{[Mathematical expression 6]}$$

Here, $\theta_B$ denotes the Brewster's angle, $n_a$ denotes the refractive index of air, and $n_p$ denotes the refractive index of the prism.

If prism angle 2 32*b* $\theta_{p2}$ is 90°, prism angle 1 32*a* $\theta_{p1}$ and prism angle 3 32*c* $\theta_{p3}$ are defined as shown in mathematical expression 7.

$$\theta_{p1} + \theta_{p3} = 90° \quad \text{[Mathematical expression 7]}$$

As described above, the relation among the prism angle 1 32*a* $\theta_{p1}$ prism angle 2 32*b* $\theta_{p2}$, and prism angle 3 32*c* $\theta_{p3}$ is defined as shown in mathematical expression 8.

$$\theta_{p3} = \theta_{p1} + \theta_B \quad \text{[Mathematical expression 8]}$$

Using mathematical expressions 7 and 8 described above, prism angle 1 32*a* $\theta_{p1}$ and prism angle 3 32*c* $\theta_{p3}$ can be obtained as shown in mathematical expressions 9 and 10.

$$\theta_{p1} = (90° - \theta_B)/2 \quad \text{[Mathematical expression 9]}$$

$$\theta_{p3} = (90° + \theta_B)/2 \quad \text{[Mathematical expression 10]}$$

Here, $\theta_B$ is the Brewster's angle.

(An Embodiment of the Prism According to the Invention)

When refractive indexes of respective parts are $n_a=1$, $m_s=1.33$, and $n_p=1.515$, it is given that the Brewster's angle is $\theta_B = \arctan(1/1.515) = 33.4°$, prism angle 1 32*a* is $\theta_{p1} = 28.3°$, and prism angle 3 32*c* is $\theta_{p3} = 61.7°$ if the refractive indexes are applied.

The degree of the critical angle according to mathematical expression 2 is $\theta_c = 61.39°$, and since the prism angle 3 32*c* $\theta_{p3}3 = 61.7°$ is greater than the critical angle, evanescent waves 73 are generated due to the total internal reflection. At this point, transmission through the prism 30 is accomplished at the Brewster's angle after total internal reflection.

As described above, since prism angle 2 32*b* $\theta_{p2}$ of the prism 30 is formed to be 90°, all the conditions for removing shadowed portions can be satisfied.

(Principles of Operation for Using the Prism According To the Invention)

When fluorescent material is excited due to the evanescent waves generated on conditions of total internal reflection and the total-internal-reflected light generating the evanescent waves passes through the prism 30, the total-internal-reflected light is transmitted at a Brewster's angle. Therefore, the components re-reflected into the prism 30 are removed, and thus the signal-to-noise ratio is improved in the present invention.

In order to reduce thickness of the prism 30 that generates the evanescent waves based on the total internal reflection, the prism 30 is miniaturized and formed as a pattern. At this point, in order to efficiently use the amount of incident light and the sample surface 43, the light should enter the prism 30 not through the transmission surface 31*b*, or the transmission surface 31*b* should not cast a shadow.

To this end, the prism is manufactured such that the incident surface 31*a* of the prism 30 is perpendicular to the propagation direction of the incident light, and the transmission surface 31*b* of the prism 30 is parallel to the proceeding direction of the incident surface. That is, the angle of the portions that do not contact with the sample surface 43 among the three internal angles of the prism is implemented to be 90°.

In order to improve the signal-to-noise ratio, the angle of the prism 30 contacting with the sample surface 43 is determined to pass the total-internal-reflected excitation light 7 through the prism 30 into the direction of the Brewster's angle with respect to the transmission surface 31*b* of the prism 30.

Since the Brewster's angle exists only with respect to the component linearly polarized into the direction parallel to the incident plane of the incident surface 31*a* among the polarized components of the incident light described above, it is preferable to install a linear polarizer 22 between the prism 30 and the light source 20 so that the polarization state of the excitation light 72 is parallel to the incident plane of the incident surface 31a.

It is configured such that emissive light of a spherical waveform coming out of the light source 20 is rendered into collimated light of a plane wave using a collimating optical device 21 and the collimated light enters into the incident surface 31a of the prism 30 in the vertical direction.

Configuration of a Fluorescence Detection Apparatus>

Figure 2:
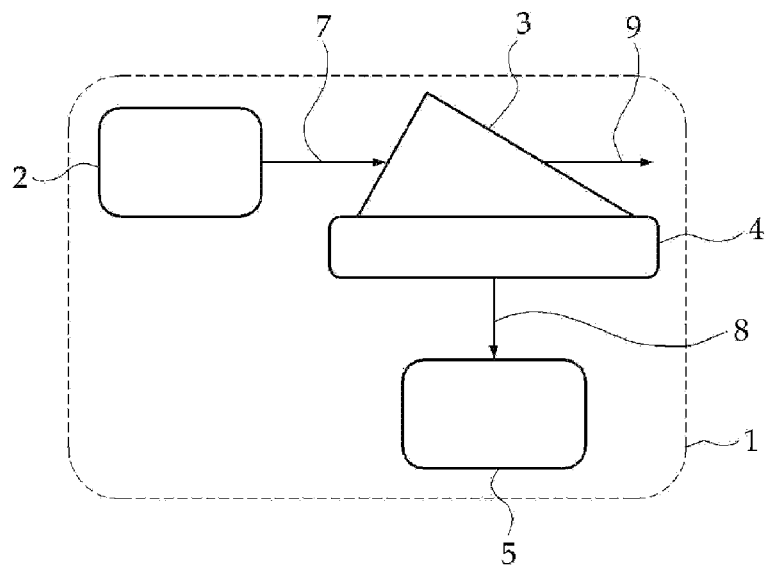
FIG. 2 is a view schematically showing the configuration of a fluorescence detection apparatus for improving a signal-to-noise ratio using evanescent waves of the prism for inducing Brewster's angle transmission according to the present invention.
Figure 3:
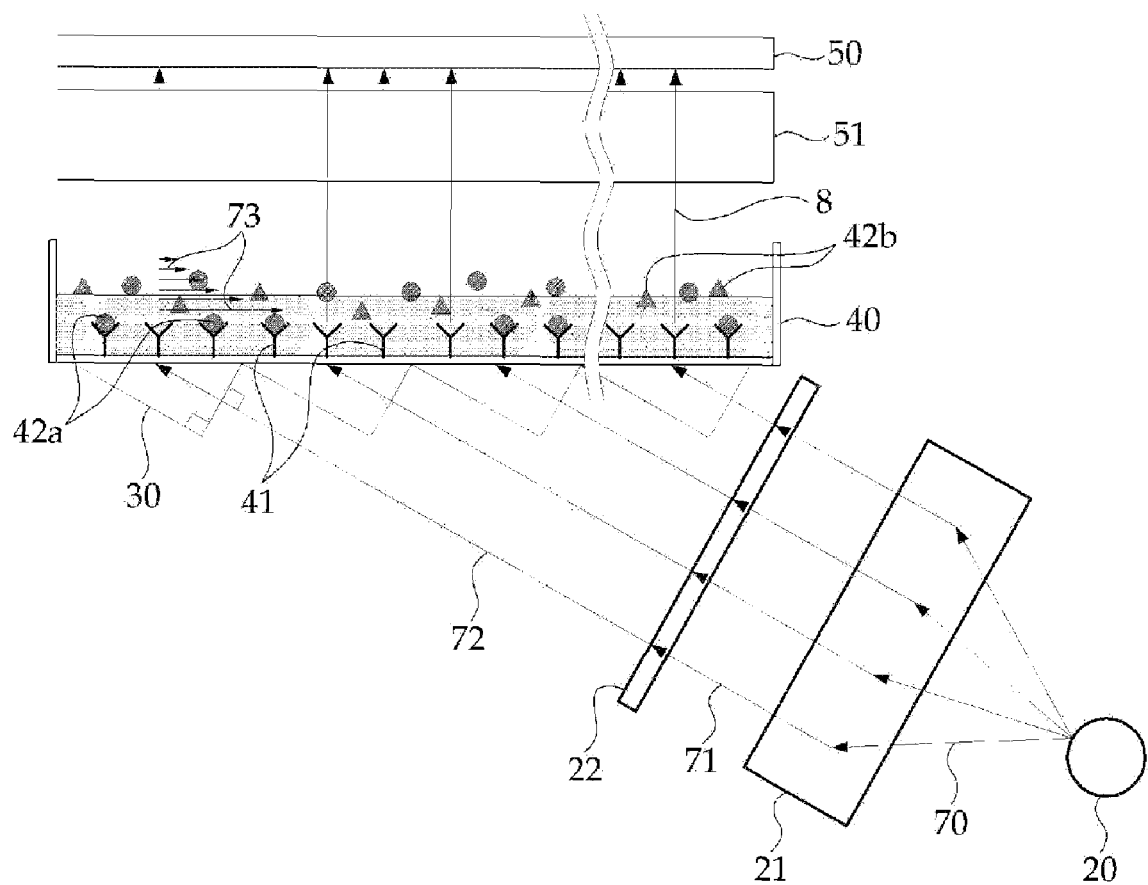
FIG. 3 is a view showing the operational state of the major portions of a fluorescence detection apparatus for improving a signal-to-noise ratio using evanescent waves of the prism for inducing Brewster's angle transmission according to the present invention.

FIG. 2 is a view schematically showing the configuration of a fluorescence detection apparatus for improving a signal-to-noise ratio using evanescent waves of the prism for inducing Brewster's angle transmission according to the present invention. FIG. 3 is a view showing the operational state of the major portions of a fluorescence detection apparatus for improving a signal-to-noise ratio using the prism for inducing Brewster's angle transmission according to the present invention. As shown in FIGS. 2 and 3, the fluorescence detection apparatus 1 comprises a light source unit 2, a prism unit 3, a sample unit 4, and a detection unit 5.

In addition, the light source unit 2 provides excitation light 7 to the prism unit 3, and the prism unit outputs transmitted light 9 passing through the prism unit 9. The sample unit 4 provides fluorescence detection light 8 to the detection unit 5.

The light source unit 2 for providing a light source 20 comprises the light source 20, a collimating optical device 21, and a linear polarizer 22. The light source 20 provides emissive light 70.

The collimating optical device 21 is formed at one side of the light source 20 to provide collimated light 71, which is preferably formed to input the collimated light 71 into the direction perpendicular to the incident surface 31a of the prism 30.

The linear polarizer 22 is formed at one side of the collimating optical device 21 to provide excitation light 72. The linear polarizer 22 is preferably formed between the prism 30 and the collimating optical device 21 in parallel to the incident surface 31a of the prism 30. That is, the direction of linear polarization of the linear polarizer 22 is formed in parallel to the incident plane of the prism 30.

Here, the incident surface is a boundary surface into which light is inputted, and the incident plane is a virtual plane formed by the propagation directions of the incident light and the reflected light, which is perpendicular to the incident surface.

The prism unit 3 is formed at one side of the light source unit 2. The prism unit 3 generates evanescent waves 73 through the total internal reflection, in which prisms are formed on the sample surface 43 of the sample unit 4.

In the prism unit 3 described above, a plurality of prisms 30 is iteratively arranged on the sample surface 43 formed on the bottom of a sample-measuring tube 40.

The sample unit 4 is formed at one side of the prism unit 3. The sample unit 4 provides fluorescence protein and a sample applied with the fluorescence protein, which forms the sample-measuring tube 40. The sample-measuring tube 40 is a place where a fluorescent reaction occurs between the fluorescence protein and the sample by the evanescent waves 73.

The detection unit 5 is formed at one side of the sample unit 4. The detection unit 5 detects the amount of fluorescence according to the reaction of the fluorescence protein and sample using the evanescent waves.

The detection unit 5 comprises an optical device 51 and a detector 50. The optical device 51 is formed at one side of the sample-measuring tube 40 of the sample unit 4, through which fluorescence detection light 8 provided by the sample-measuring tube 40 passes. The detector 50 is formed at one side of the optical device 51 and detects the amount of fluorescence of the fluorescence detection light 8 provided by the optical device 51.

(Operation of the Fluorescence Detection Apparatus)

FIG. 3 shows an embodiment of the fluorescence detection apparatus according to the present invention. Emissive light 70 coming out of the light source 20 becomes collimated light 71 according to the range of measurement while passing through the collimating optical device 21.

The collimated light 71 becomes excitation light 72 after passing through the linear polarizer 22 arranged in parallel to the incident plane. The light source unit 2 allows the light coming out of the light source 20 to be entered at an angle greater than the critical angle within the pattern of the prism 30 through angular alignment.

The fluorescent protein 41 for detecting special materials, which is applied on the sample surface 43 of the sample-measuring tube 40, is excited by the evanescent waves 73 generated by the total internal reflection and generates fluorescent detection light 8. Degree of reaction to the fluorescent protein 41 for detecting special material is varied depending on the amount of desired component 42a in the measured sample 42 put in the sample-measuring tube 40, and the amount of fluorescent of the excited fluorescent detection light 8 is changed accordingly.

If the fluorescent detection light 8 arrives at the detector 50 through the optical device 51, the detector 50 calculates the amount of fluorescent.

The pattern of the prism 30 makes the inducing medium thin by miniaturizing and repeatedly arranging the prisms 30 having a certain shape. Each of the prisms 30 has a certain shape as described above with reference to FIG. 1.

In this manner, the prisms 30 can be manufactured by respectively adjusting prism angles 32a, 32b, and 32c of each the prism 30 depending on the refraction indexes of the measured sample and the inducing medium 1.

In the present invention, the evanescent waves generated when light is radiated onto the fluorescent material applied on the sample surface at an angle greater than the critical angle is used as excitation light of the fluorescent so that the incident light may pass through the prism in the direction of the Brewster's angle after total internal reflection.

Accordingly, the signal-to-noise ratio is improved by removing re-reflection of the light into the prism, and the volume of the prism can be reduced by miniaturizing and patterning the prism. Therefore, the present invention can be used to increase usage of the sample area and efficiency of the light amount.

Effects of the present invention described above are as follows.

First, the present invention is effective in that fluorescent can be detected using evanescent waves of the prism for inducing Brewster's angle transmission.

Second, the present invention is effective in that the prism for inducing Brewster's angle transmission can be miniaturized.

Third, the present invention is effective in that a prism can be formed thinner, while uniformly radiating a wide sample area, by designing the prism not to interfere with excitation light entered into the prism in parallel to neighboring prisms and repeatedly arranging the prisms.

Fourth, the present invention is effective in that the entire sample surface can be used without connection to the loss rate of the light amount by miniaturizing and repeatedly arranging the prisms.

Fifth, the present invention is effective in that the degree of reaction of each sample surface does not affect the amount of excitation light of neighboring samples by repeatedly arranging small prisms on the entire sample surface and irradiating collimated light onto excite fluorescent material.

Sixth, the present invention is effective in that a signal-to-noise ratio can be improved by removing components re-reflected into the prism and passing through the sample surface, which is accomplished by inducing total-internal-reflected light to pass through the prism at a Brewster's angle after generating evanescent waves.

While the present invention has been described with reference to the particular illustrative embodiments, it is not to be restricted by the embodiments but only by the appended claims. It is to be appreciated that those skilled in the art can change or modify the embodiments without departing from the scope and spirit of the present invention.

What is claimed is:

1. A prism for inducing Brewster's angle transmission, wherein light linearly polarized in parallel to an incident plane is induced to enter the prism, generate evanescent waves by total internal reflection, and pass through the prism at a Brewster's angle so as not to have a component that is re-reflected into the prism and passes through a sample surface, the prism comprising:
    an incident surface formed at a first end on a lower side of the sample surface and a transmission surface formed at a second end on the lower side from a viewpoint of a side cross-sectional direction, wherein the incident surface is perpendicular to the transmission surface at a contacting position.

2. The prism according to claim 1, wherein the incident surface of the prism is formed to be perpendicular to an incident angle of excitation light.

3. The prism according to claim 2, wherein an angle between the incident surface and the transmission surface of the prism is formed as prism angle 2, and the prism angle 2 is 90°.

4. The prism according to claim 2, wherein an angle between the sample surface and the transmission surface of the prism is formed as prism angle 1, and the prism angle 1 is formed by mathematical expression $\theta_{p1}=(90°-\theta_B)/2$, wherein $\theta_B$ is the Brewster's angle.

5. The prism according to claim 2, wherein an angle between the sample surface and the incident surface is formed as prism angle 3, and the prism angle 3 is formed by mathematical expression $\theta_{p3}=(90°+\theta_B)/2$, wherein $\theta_B$ is the Brewster's angle.

6. The prism according to claim 3, wherein the Brewster's angle is formed by mathematical expression $\theta_B=\arctan(n_a/n_p)$, wherein in $n_a$ is a refractive index of air, and $n_p$ is a refractive index of the prism.

7. A fluorescence detection apparatus using evanescent waves of a prism for inducing Brewster's angle transmission, the prism being configured in accordance with claim 1, the apparatus comprising:
    a light source unit for providing a light source;
    a prism unit formed at one side of the light source unit and having a prism for generating the evanescent waves by total internal reflection;
    a sample unit formed at one side of the prism unit and having a sample-measuring tube for providing fluorescent protein and a sample applied with the fluorescent protein; and
    a detection unit formed at one side of the sample unit, for detecting an amount of fluorescent depending on a reaction of the fluorescent protein and the sample using the evanescent waves.

8. The apparatus according to claim 7, wherein the light source unit comprises:
    the light source for providing emissive light;
    a collimating optical device formed at one side of the light source, for providing collimated light; and
    a linear polarizer formed at one side of the collimating optical device, for providing excitation light.

9. The apparatus according to claim 7, wherein the collimating optical device is formed to input the collimated light in a direction perpendicular to an incident surface of the prism.

10. The apparatus according to claim 7, wherein the linear polarizer is formed between the prism and the collimating optical device to be parallel to the incident surface of the prism.

11. The apparatus according to claim 7, wherein the prism unit is formed to repeatedly arrange a plurality of prisms on the sample surface formed on a bottom of the sample-measuring tube.

12. The apparatus according to claim 7, wherein the detection unit includes:
    an optical device formed at one side of the sample-measuring tube of the sample unit, for passing through fluorescent detection light provided by the sample-measuring tube; and
    a detector for calculating the fluorescent detection light provided by the optical device.

* * * * *